United States Patent
Peña Hueso et al.

(10) Patent No.: US 9,917,328 B2
(45) Date of Patent: Mar. 13, 2018

(54) HALOGENATED ORGANOSILICON ELECTROLYTES, METHODS OF USING THEM, AND ELECTROCHEMICAL DEVICES CONTAINING THEM

(71) Applicant: Silatronix, Inc., Madison, WI (US)

(72) Inventors: José Adrián Peña Hueso, Madison, WI (US); Jian Dong, Fort Collins, WI (US); Michael L. Pollina, Johnson Creek, WI (US); Monica L. Usrey, Madison, WI (US); Robert J. Hamers, Madison, WI (US); Robert C. West, Madison, WI (US); David Osmalov, Monona, WI (US)

(73) Assignee: Silatronix, Inc., Madison, WI (US)

( * ) Notice: Subject to any disclaimer, the term of this patent is extended or adjusted under 35 U.S.C. 154(b) by 323 days.

(21) Appl. No.: 14/374,734

(22) PCT Filed: Feb. 4, 2013

(86) PCT No.: PCT/US2013/024629
§ 371 (c)(1),
(2) Date: Jul. 25, 2014

(87) PCT Pub. No.: WO2013/116836
PCT Pub. Date: Aug. 8, 2013

(65) Prior Publication Data
US 2015/0037686 A1 Feb. 5, 2015

Related U.S. Application Data

(60) Provisional application No. 61/594,672, filed on Feb. 3, 2012.

(51) Int. Cl.
*H01M 10/0567* (2010.01)
*C07F 7/12* (2006.01)
(Continued)

(52) U.S. Cl.
CPC ....... *H01M 10/0567* (2013.01); *C07F 7/0852* (2013.01); *C07F 7/12* (2013.01);
(Continued)

(58) Field of Classification Search
CPC .... H01M 6/14–6/188; H01M 10/056–10/0569
See application file for complete search history.

(56) References Cited

U.S. PATENT DOCUMENTS 5,120,406 A 6/1992 Shono et al.
2005/0106470 A1* 5/2005 Yoon et al. .................. 429/324
(Continued)

FOREIGN PATENT DOCUMENTS

CN 101820082 A 9/2010
EP 0446578 A2 9/1991
WO WO 2011/153854 A1 12/2011

*Primary Examiner* — Jonathan G Leong
(74) *Attorney, Agent, or Firm* — Joseph T. Leone, Esq.; DeWitt Ross & Stevens S.C.

(57) ABSTRACT

Described are electrolyte compositions having at least one salt and at least one compound selected from the group consisting of: wherein "a" is from 1 to 3; "b" is 1 or 2; 4≥"a"+"b"≥2; X is a halogen; R can be alkoxy or substituted alkoxy, among other moieties, and R¹ is alkyl, substituted alkyl, aryl, substituted aryl, alkoxy, or substituted alkoxy. Also described are electrochemical devices that use the electrolyte composition.

13 Claims, 9 Drawing Sheets

(51) Int. Cl.
  *H01M 10/052*   (2010.01)
  *H01M 10/0564*  (2010.01)
  *C07F 7/08*     (2006.01)
  *H01M 4/131*    (2010.01)
  *H01M 10/0525*  (2010.01)
  *H01M 10/0565*  (2010.01)
  *H01M 4/02*     (2006.01)

(52) U.S. Cl.
  CPC ............ *C07F 7/123* (2013.01); *H01M 4/131* (2013.01); *H01M 10/052* (2013.01); *H01M 10/0525* (2013.01); *H01M 10/0564* (2013.01); *H01M 10/0565* (2013.01); *H01M 2004/028* (2013.01); *H01M 2300/0025* (2013.01); *H01M 2300/0065* (2013.01)

(56) References Cited

U.S. PATENT DOCUMENTS

| | | |
|---|---|---|
| 2006/0083992 A1 | 4/2006 | Nakanishi et al. |
| 2007/0059597 A1 | 3/2007 | Nakanishi et al. |
| 2007/0243470 A1* | 10/2007 | Yamamoto ........ H01M 10/0567 429/326 |
| 2009/0286157 A1 | 11/2009 | Chen et al. |
| 2010/0015514 A1 | 1/2010 | Miyagi et al. |
| 2013/0084490 A1* | 4/2013 | Zhang et al. ................ 429/188 |

* cited by examiner

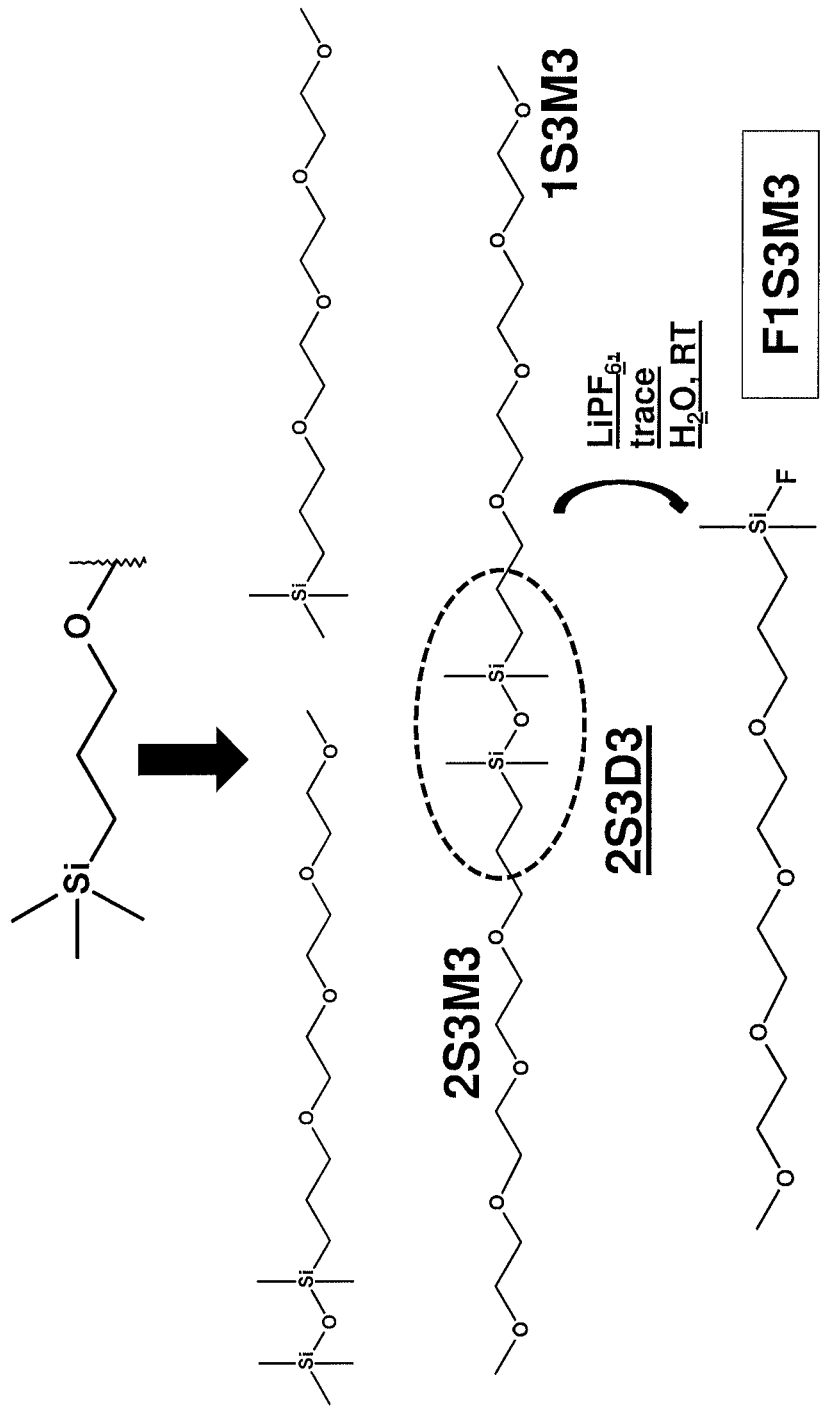

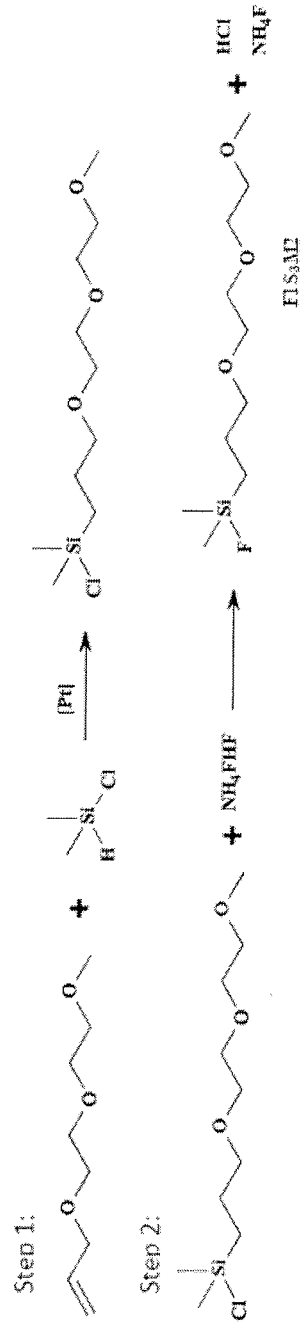
FIG.2: Synthesis of F1S₃M2

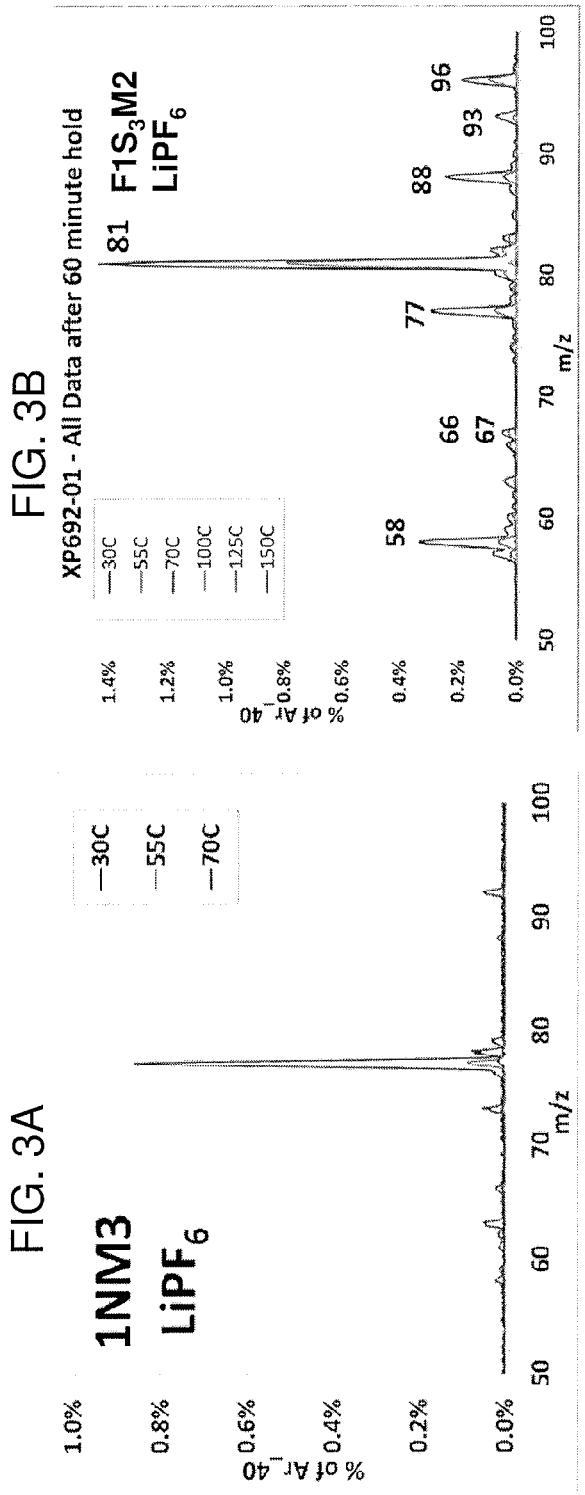
FIGS. 3A & 3B: Thermal Stability of F1S₃M2 and 1NM3

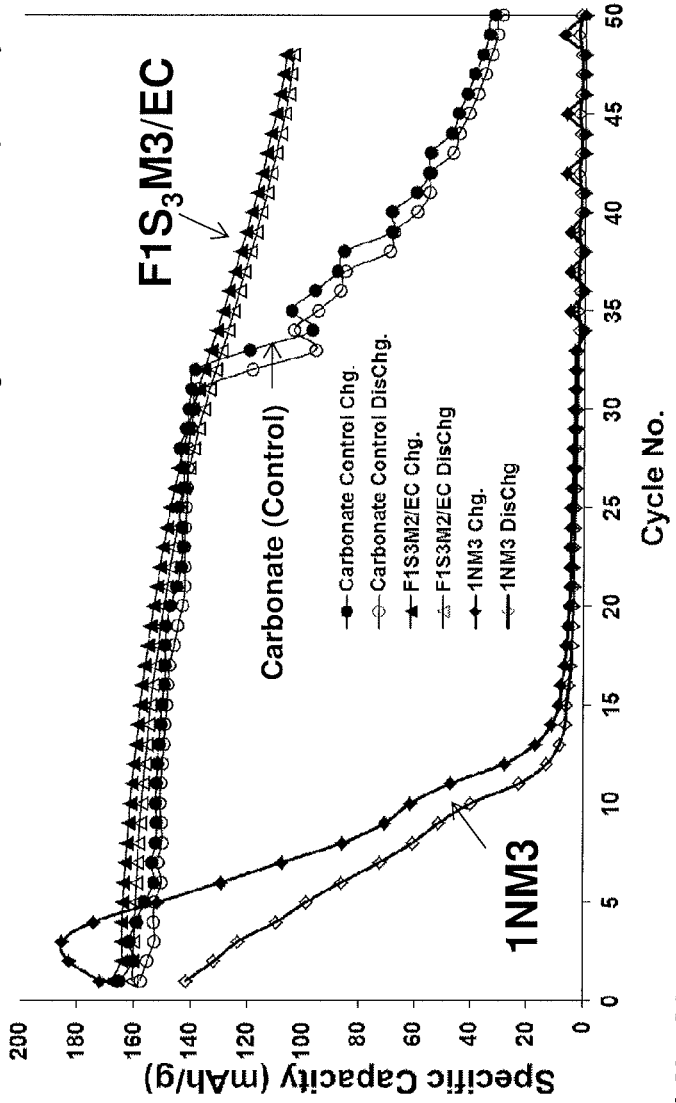

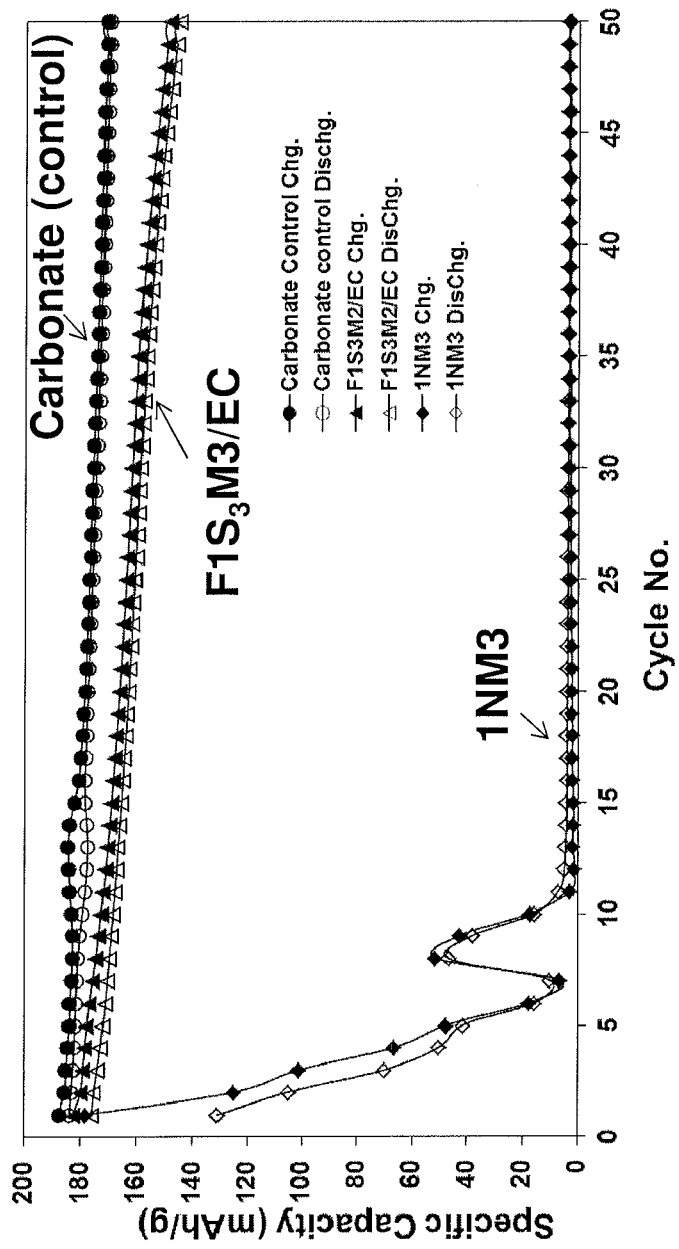

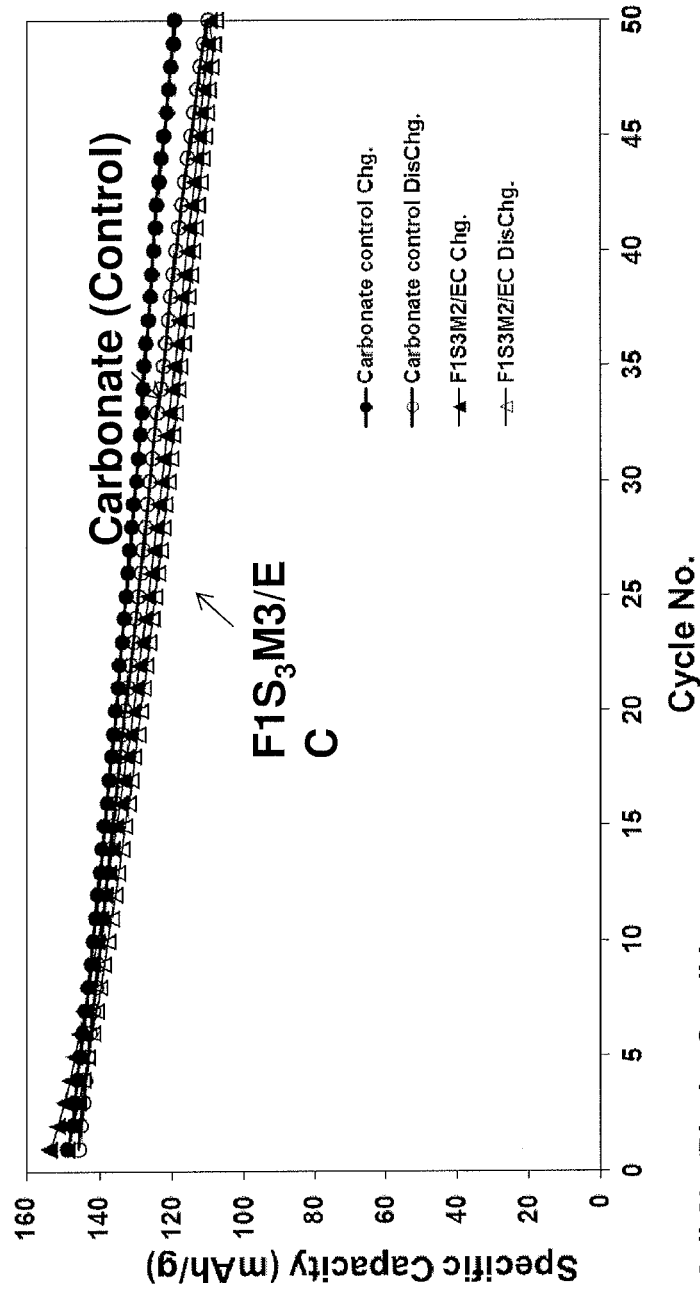

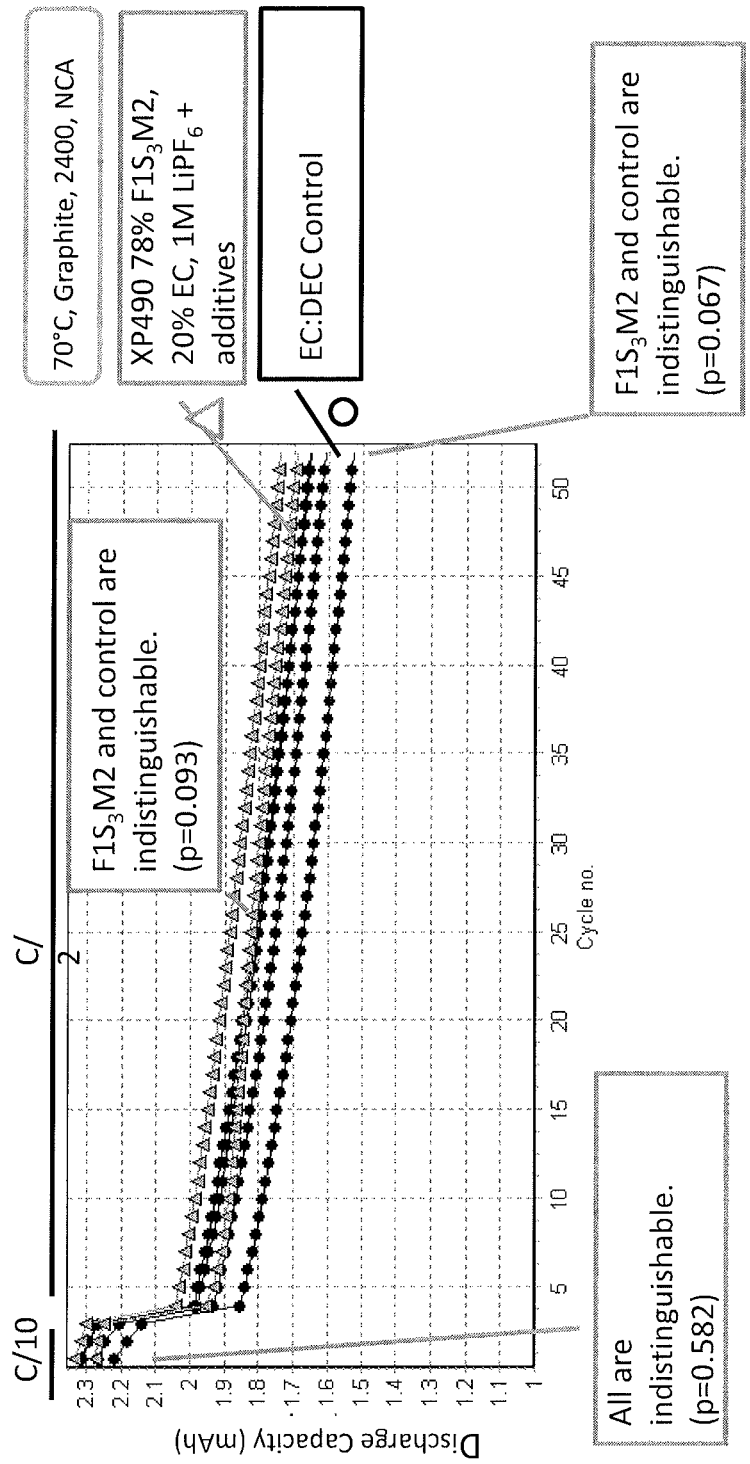
FIG.7: Full Cell Cycling of F1S₃M2 at 70 °C (NCA)

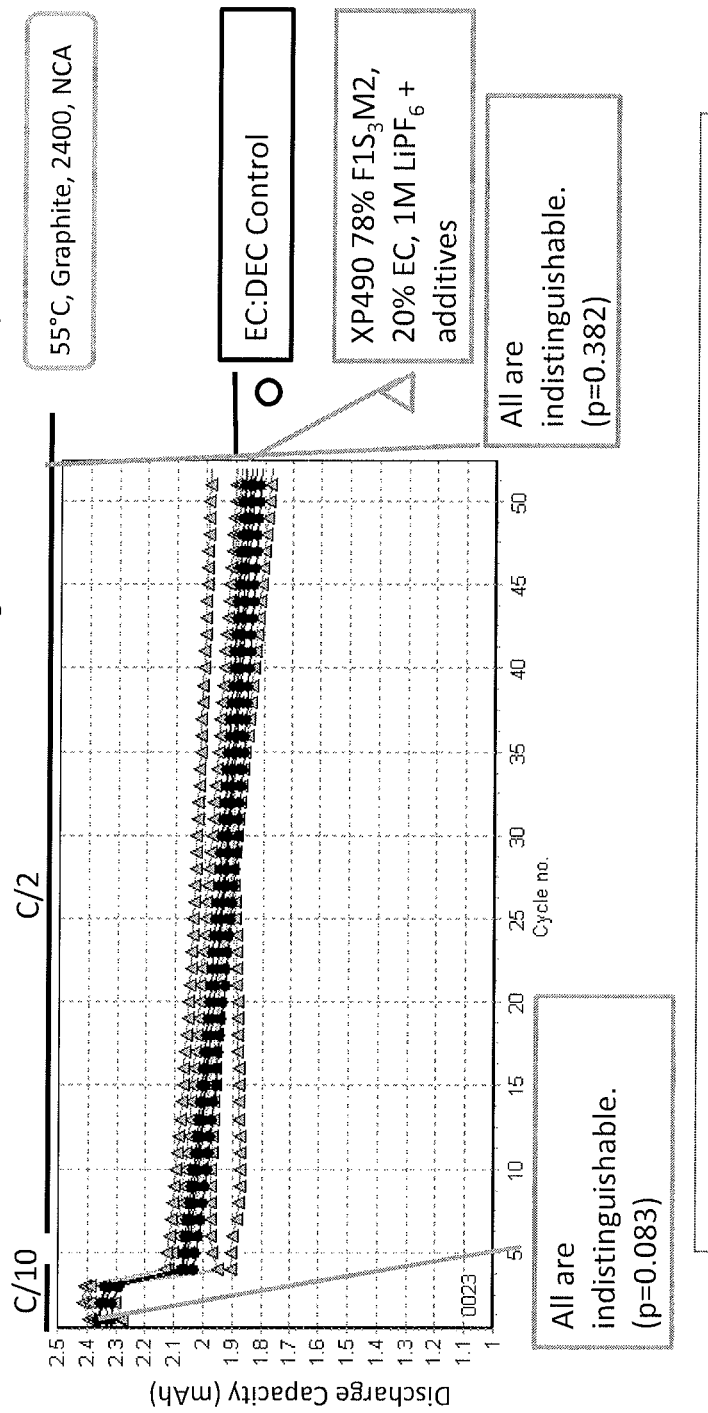

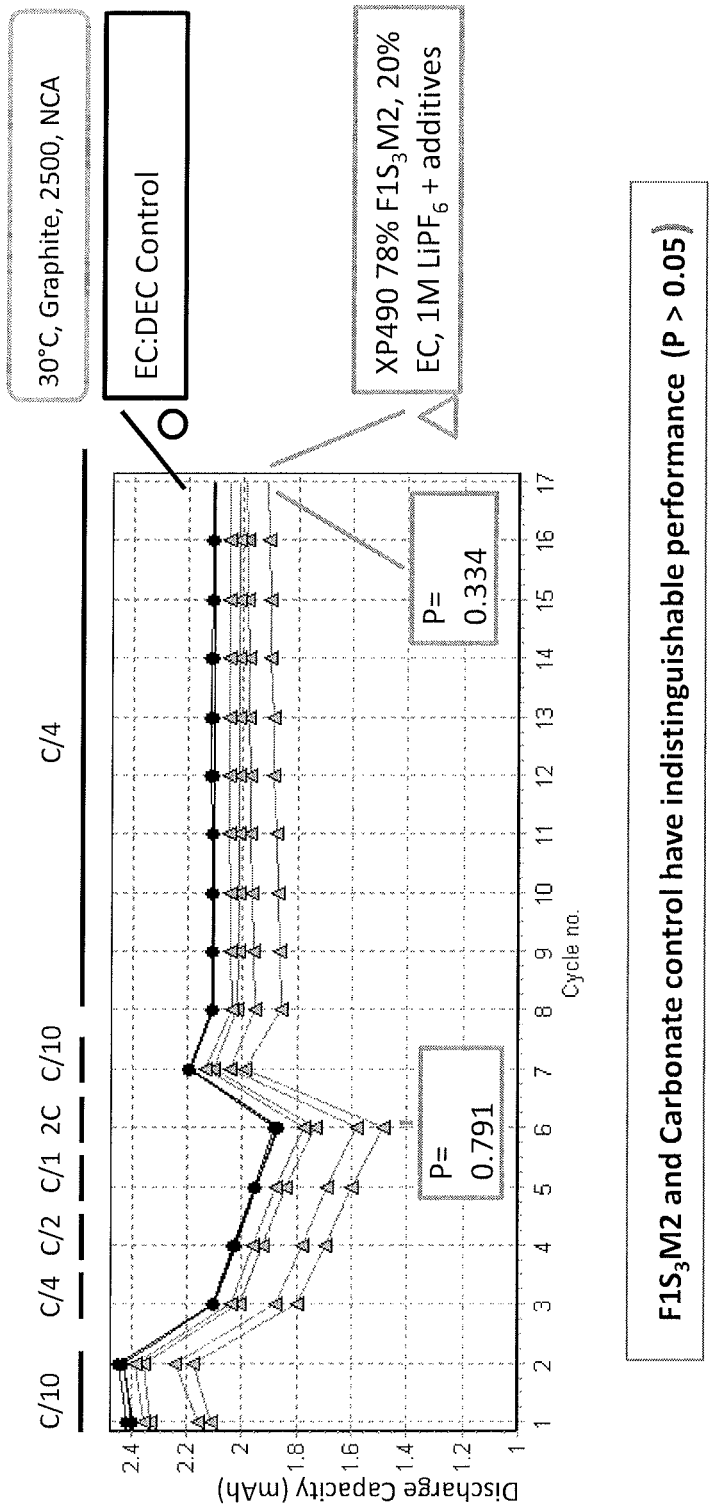

HALOGENATED ORGANOSILICON ELECTROLYTES, METHODS OF USING THEM, AND ELECTROCHEMICAL DEVICES CONTAINING THEM

CROSS-REFERENCE TO RELATED APPLICATIONS

This is a National Stage application of international application Serial No. PCT/US2013/024629, filed 4 Feb. 2013, which claims the benefit of U.S. provisional application Ser. No. 61/594,672, filed 3 Feb. 2012, both of which are incorporated herein by reference.

FEDERAL FUNDING STATEMENT

This invention was made with government support under contract number N68335-11-C-0401 awarded by the Naval Air Warfare Center. The government has certain rights in the invention.

BACKGROUND

A variety of primary batteries employ electrolytes with organic solvents such as diethyl carbonate (DEC) and ethylene carbonate (EC). These batteries are often stored for extended periods of time before use. However, the performance of these batteries often drops after this storage. For instance, the capacity of these batteries often decreases after extended storage. Additionally, the pulsing capability of these batteries can drop after storage.

Rechargeable lithium batteries are widely discussed in the literature and are readily commercially available. They typically consist of a positive electrode and a negative electrode spaced by a separator, an electrolyte, a case, and feedthrough pins respectively connected to the electrodes and extending externally of the case. Each electrode is typically formed of a metal substrate that is coated with a mixture of an active material, a binder, and a solvent. In a typical battery design, the electrodes comprise sheets which are rolled together, separated by separator sheets, and then placed in a prismatic case. Positive and/or negative feed through pins (i.e., terminals) are then connected to the respective electrodes and the case is sealed.

The negative electrode is typically formed of a copper substrate carrying graphite as the active material. The positive electrode is typically formed of an aluminum substrate carrying lithium cobalt dioxide as the active material. The electrolyte is most commonly a 1:1 mixture of EC:DEC in a 1.0 M salt solution of $LiPF_6$. The separator is frequently a micro porous membrane made of a polyolefin such as a combination of polyethylene and/or polypropylene.

The demand for lithium batteries has increased enormously in recent years. This increased demand has resulted in ongoing research and development to improve the safety and performance of these batteries. The conventional organic carbonate solvents employed in the electrolytes of many lithium ion batteries are associated with a high degree of volatility, flammability, and chemical reactivity. A variety of electrolytes that include polysiloxane solvents have been developed to address these issues.

Electrolytes that include a polysiloxane solvent typically have a low ionic conductivity that limits their use to applications that do not require high rate performance. Additionally, batteries that include conventional polysiloxane solvents have shown poor cycling performance when used in secondary batteries. As a result, lithium bis-oxalato borate (LiBOB) has been used as the salt in these electrolytes. While LiBOB improves the performance of the batteries, LiBOB is unstable in the presence of water. The amount of moisture in battery electrolytes and/or electrodes can be on the order of several hundred ppm. The presence of this moisture can cause LiBOB to decompose into lithium oxalate ($LiHC_2O_4 \cdot H_2O$) and form a precipitate in the electrolyte. This precipitate tends to increase the internal resistance of electrical devices such as batteries.

Thus there remains a long-felt and unmet need to increase the performance, safety, and storage life of lithium-based batteries and other electrical charge-storing devices.

SUMMARY OF THE INVENTION

Disclosed herein is an electrolyte composition comprising at least one salt and at least one compound selected from the group consisting of:

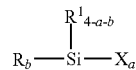

wherein subscript "a" is an integer of from 1 to 3;
subscript "b" is 1 or 2; and
4≥"a"+"b"≥2;
X is a halogen;
R is selected from the group consisting of alkoxy, substituted alkoxy, Formula 1 moieties, and Formula II moieties:

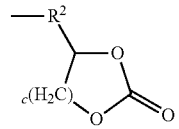

Formula I

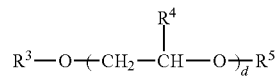

Formula II wherein $R^2$ is an organic spacer;
$R_3$ is nil or an organic spacer;
$R^4$ is hydrogen, alkyl, or aryl;
$R^5$ is alkyl or aryl;
subscript "c" is 1 or 2; and
subscript "d" is from 1 to 12; and
$R^1$ is selected from the group consisting of alkyl, substituted alkyl, aryl, substituted aryl, alkoxy, and substituted alkoxy.

In one version of the electrolyte composition X is chlorine, fluorine, or bromine. In another version of the electrolyte composition, X is fluorine. In certain versions of the electrolyte composition, "a" is 1, "b" is 1, and $R^1$ is $C_1$ to $C_{10}$ alkyl. In still other versions of the electrolyte composition, $R^1$ is methyl.

In yet another version of the composition, R is substituted or unsubstituted lower alkoxy, and $R^1$ is substituted lower alkyl or lower alkoxy.

In any version of the composition described herein, at least one salt may be a lithium-containing salt. At least one salt may be present in a concentration of from about 0.1 M to about 3.5 M. Concentrations above and below 0.1 M to 3.5 M are explicitly within the scope of the composition described and claimed herein.

In any version of the composition described herein, at least one salt may be selected from the group consisting of LiClO$_4$, LiBF$_4$, LiAsF$_6$, LiPF$_6$, LiCF$_3$SO$_3$, Li(CF$_3$SO$_2$)$_2$N, Li(CF$_3$SO$_2$)$_3$C, Li(C$_2$F$_5$ SO$_2$)$_2$N, LiDFOB, LiBOB, lithium alkyl fluorophosphates, lithium borates and lithium bis(chelato)borates. Other salts are within the scope of the composition described and claimed herein. This list is by way of example only and not limitation.

The electrolyte composition may be a liquid, a gel, or a solid.

Also described herein is an electrochemical device characterized in that it includes an electrolyte composition as recited as described and claimed herein. The electrochemical device may include an anode and the electrolyte composition may further be characterized in that it forms a passivation layer on the anode. In one version, the device is a lithium secondary battery comprising at least one lithium metal oxide cathode and at least one anode.

The compounds described herein are also part of the invention. Thus, disclosed herein are compounds selected from the group consisting of:

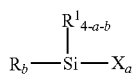

wherein subscript "a" is an integer of from 1 to 3; subscript "b" is 1 or 2; and 4≥"a"+"b"≥2; X is a halogen; R is selected from the group consisting of alkoxy, substituted alkoxy, Formula 1 moieties, and Formula II moieties:

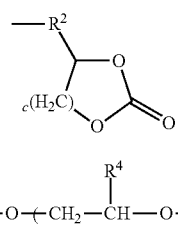

Formula I

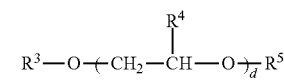

Formula II wherein R$^2$ is an organic spacer; R$_3$ is nil or an organic spacer; R$^4$ is hydrogen, alkyl, or aryl; R$^5$ is alkyl or aryl; subscript "c" is 1 or 2; and subscript "d" is from 1 to 12; and R$^1$ is selected from the group consisting of alkyl, substituted alkyl, aryl, substituted aryl, alkoxy, and substituted alkoxy.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

BRIEF DESCRIPTION OF THE DRAWINGS

FIG. 1 is a reaction scheme depicting how to make one of the preferred organosilicon compounds. As depicted, the compound F1S3M3 includes a silicon atom to which is bonded a fluorine (F1), two methyl groups, a trimethylene spacer (S3), and three (3) polyethylene oxide units in tandem (M3).

FIG. 2 is a graph depicting the synthesis of F1S3M2, a homolog of the F1S3M3 compound depicted in FIG. 1. As shown in FIG. 2, the compound F1S3M2 includes a silicon atom to which is bonded a fluorine (F1), two methyl groups, a trimethylene spacer (S3), and two (2) polyethylene oxide units in tandem (M2).

FIGS. 3A and 3B are graphs depicting the thermal stability of 1NM3 (FIG. 3A) and F1S3M2 (FIG. 3B). As noted in the figure, F1S3M2 displayed less than 5% decomposition after heating to 150° C. in the present of 1M LiPF$_6$.

FIG. 4 is a graph depicting half cell cycling performance of compound F1S3M3 as shown in FIG. 1, at 70° C., using a NMC cathode. The X-axis records cycle number, the Y-axis records specific capacity in mAhg. The specifics of the charge-discharge cycle and anode/cathode construction are recorded at the bottom of the figure. ("NMC"=Nickel Magnesium Cobalt; "CCCV"=constant current, constant voltage. NMC cathodes are available from many commercial suppliers, such as Targray Inc., Laguna Niguel, Calif., USA; "W-Scope" film is a commercial, proprietary separator sold by W-Scope Corporation, Kawasaki, Japan.)

FIG. 5 is a graph depicting half cell cycling performance of compound F1S3M3 at 70° C. using a NCA cathode. The X-axis records cycle number, the Y-axis records specific capacity in mAhg. The specifics of the charge-discharge cycle and anode/cathode construction are recorded at the bottom of the figure. ("NCA"=Nickel Cobalt Aluminum. NCA cathodes are commercially available from numerous sources, including Targray Inc. "Celgard 2400" is a monolayer polypropylene-based separator available commercially from Celgard LLC, Charlotte, N.C., USA.)

FIG. 6 is a graph depicting full cell cycling performance of compound F1S3M3 at 70° C. using a NMC cathode. The X-axis records cycle number, the Y-axis records specific capacity in mAhg. The specifics of the charge-discharge cycle and anode/cathode construction are recorded at the bottom of the figure. ("EC"=ethylene carbonate; "DEC"=diethyl carbonate.)

FIG. 7 is a graph depicting full cell cycling performance of F1S3M2 at 70° C. using a NCA cathode. The X-axis records cycle number, the Y-axis records discharge capacity in mAh.

FIG. 8 is a graph depicting full cell cycling performance of F1S3M2 at 55° C. using a NCA cathode. The X-axis records cycle number, the Y-axis records discharge capacity in mAh. This graph compares using EC:DEC as the electrolyte versus 78% F1S3M220% EC/1M LiPF$_6$.

FIG. 9 is a graph comparing discharge rates at 30° C. between F1S3M2 as compared to carbonate using a NCA cathode. As noted in the figure, the two are indistinguishable.

DETAILED DESCRIPTION

The present disclosure relates to an electrolyte composition containing at least one halogenated organosilicon solvent, and an electrochemical device characterized by including the electrolyte composition. The preferred electrochemical device is a lithium secondary battery comprising the electrolyte composition described herein. More specifically, described herein is an electrolyte composition that is moisture-resistant, non-flammable, has a wide temperature-operation window, and is far safer as compared to conventional electrolytes. Moreover, the electrolyte composition disclosed herein has improved capacity retention properties, voltage stability and durability when incorporated into a lithium secondary battery or other lithium-ion charge storage devices.

It has been discovered by the named co-inventors that fluorinated organosilicon compounds are non-hydrolyzable at room temperature. Thus, the resulting electrolytes have a much higher tolerance for moisture. Simultaneously, the voltage stability of the organosilicon compounds described herein is greatly improved, presumably due to the effect of halogen substitutions. The electrolyte compositions described herein, which are halogenated organosilicon solvents (generally liquids, but can also be solid) are non-flammable, offer improved safety and higher voltage windows than conventional electrolytes, and provide a unique solid electrolyte interphase (SEI) film on the graphite anode, resulting in better performance and cell capacity. Cells using the electrolyte compositions described herein improve capacity retention, voltage and thermal stability, and can be operated over a wide temperature window—most notably at elevated temperatures.

As used herein, the term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C_1$-$C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs, and isomers thereof, for example, n-pentyl, n-hexyl, n-heptyl, n-octyl, and the like. The term "alkyl," unless otherwise noted, also includes "cycloalkyl."

The term "alkenyl" means an alkyl group as defined above containing one or more double bonds. Examples of alkenyl groups include vinyl, 2-propenyl, crotyl, 2-isopentenyl, 2-butadienyl, 2,4-pentadienyl, 1,4-pentadienyl, etc., and higher homologs and isomers.

The term "alkynyl" means an alkyl or alkenyl group as defined above containing one or more triple bonds. Examples of alkynyl groups include ethynyl, 1- and 3-propynyl, 3-butynyl, and the like, including higher homologs and isomers.

The terms "alkylene," "alkenylene," and "alkynylene," alone or as part of another substituent means a divalent radical derived from an alkyl, alkenyl, or alkynyl group, respectively, as exemplified by —$CH_2CH_2CH_2CH_2$—.

Typically, alkyl, alkenyl, and alkynyl groups (as well as alkylene, alkenylene, and alkynylene groups) will have from 1 to 36 carbon atoms, although longer alkyl groups are explicitly within the scope of the term "alkyl." Those groups having 10 or fewer carbon atoms in the main chain are preferred in the present compositions, and groups of this length are collectively referred to as "lower alkyl, "lower alkenyl," etc.

The term "alkoxy" is used herein to refer to the —OR group, where R is an alkyl as defined herein or a substituted analog thereof. Suitable alkoxy radicals include, for example, methoxy, ethoxy, t-butoxy, etc. In the same fashion as "lower" with respect to alkyl, "lower alkoxy" refers to an alkoxy group of 10 or fewer carbon atoms in the main chain.

"Substituted" refers to a chemical group as described herein that further includes one or more substituents, such as lower alkyl, aryl, acyl, halogen (e.g., alkylhalo such as $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl, alkoxy, and aryl moieties. Additionally, these groups may be pendent from, or integral to, the carbon chain itself.

The term "acyl" is used to describe a ketone substituent, —C(O)R, where R is substituted or unsubstituted alkyl or aryl as defined herein. The term "carbonyl" is used to describe an aldehyde substituent. The term "carboxy" refers to an ester substituent or carboxylic acid, i.e., —C(O)O— or —C(O)—OH.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "arylalkyl" and "substituted aryl." For phenyl groups, the aryl ring may be mono-, di-, tri-, tetra-, or penta-substituted. Larger rings may be unsubstituted or bear one or more substituents.

"Substituted aryl" refers to aryl as just described including one or more functional groups such as lower alkyl, acyl, halogen, alkylhalo (e.g., $CF_3$), hydroxy, amino, alkoxy, alkylamino, acylamino, acyloxy, phenoxy, mercapto, and both saturated and unsaturated cyclic hydrocarbons which are fused to the aromatic ring(s), linked covalently or linked to a common group such as a diazo, methylene, or ethylene moiety. The linking group may also be a carbonyl such as in cyclohexyl phenyl ketone.

"Halogen" or "halo" refers to the elements of Group 17 (IUPAC-style) (formerly group VII or VIIA) of the periodic table, namely fluorine (F), chlorine (Cl), bromine (Br), iodine (I), and astatine (At).

The term "organic spacer" or "spacer" refers to a divalent group including alkylene, alkenylene, and alkynylene groups. Other suitable spacers include alkylene oxide, and bivalent ether moieties. These spacers can be substituted or unsubstituted. The above spacers can also be completely or partially halogenated. For instance, the spacers can be completely or partially fluorinated.

The electrolyte compositions comprise at least one salt and at least one compound selected from the group consisting of:

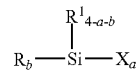

wherein subscript "a" is an integer of from 1 to 3; subscript "b" is 1 or 2; and 4≥"a"+"b"≥2. X is a halogen. R is selected from the group consisting of alkoxy and substituted alkoxy. R may also be a moiety selected from Formula 1 and/or Formula II:

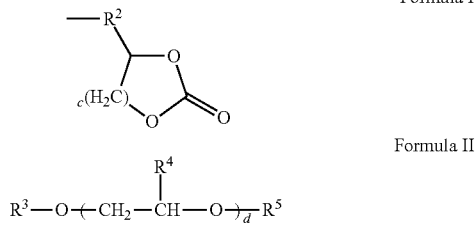

Formula I

Formula II wherein $R^2$ is an organic spacer; $R^3$ is nil or an organic spacer; $R^4$ is hydrogen, alkyl, or aryl; $R^5$ is alkyl or aryl; subscript "c" is 1 or 2; and subscript "d" is from 1 to 12.

$R^1$ is selected from the group consisting of alkyl, substituted alkyl, aryl, substituted aryl, alkoxy, and substituted alkoxy.

It is preferred that X is chlorine, fluorine, or bromine, most preferably fluorine. When X is fluorine, it is also preferred that "a" is 1, "b" is 1, and $R^1$ is $C_1$ to $C_{10}$ alkyl (and most preferably $R^1$ is methyl). In certain preferred embodiments of the composition, R is substituted or unsubstituted lower alkoxy, and $R^1$ is substituted lower alkyl or lower alkoxy.

Particularly preferred silicon-containing compounds according to the present disclosure are:

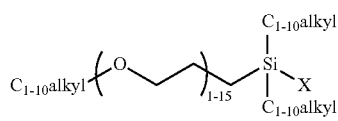

wherein X is Cl, Fl, or Br. Most preferred are those in which X is fluorine, and the $C_{1-10}$ alkyl groups are $C_6$ or smaller (and most preferably methyl). The preferred silicon-containing compounds are designated F1S3M3, and F1S3M2; F1S3M3 is depicted in FIG. 1.

It is preferred that the salt be a lithium-containing salt. From among the lithium-containing salts, $LiClO_4$, $LiBF_4$, $LiAsF_6$, $LiPF_6$, $LiCF_3SO_3$, $Li(CF_3SO_2)_2N$, $Li(CF_3SO_2)_3C$, $Li(C_2F_5 SO_2)_2N$, LiDFOB, LiBOB, lithium alkyl fluorophosphates, lithium borates and lithium bis(chelato)borates are preferred. If a lithium salt is used, preferably it is present in the composition in a concentration of from about 0.1 M to about 3.5 M. Concentrations above and below this stated range are explicitly within the scope of the present disclosure. The composition is preferably formulated to be a free-flowing liquid. However, the electrolyte may also be formulated to be a gel or a solid, depending upon the moieties selected for R and $R^1$ and the concentration of the silicon-containing compound in the electrolyte composition as a whole.

The present disclosure includes any and all electrochemical devices that comprise the electrolyte composition described and claimed herein. Such devices may optionally comprise an anode and the electrolyte composition optionally further comprises an additive dimensioned and configured to form a passivation layer on the anode. Preferred electrochemical devices are lithium secondary batteries that comprise at least one lithium metal oxide cathode and at least one anode.

Synthesis of F1S3M3:

Depicted in FIG. 1 is the preferred silicon-containing compound, which has been designated F1S3M3.

The synthesis begins with the triethyleneglycol allyl methyl ether ("TEGAME"). This is a known and common compound that can be made by several literature routes, most of which involve adding the allyl group to the glycol using allyl bromide under different conditions, and using different solvents, temperatures, times, and bases. The route used here was as follows (illustrated in Scheme 1, below):

Triethyleneglycol methyl ether (185 mL) was dissolved in 500 mL of toluene and 47.2 g of NaOH were added under vigorous stirring in a 1 L flask. When the mixture was homogenous, 143 g of allylbromide was added drop-wise using an addition funnel over a two hour period. Care was taken to ensure that the mixture did not get too hot. (If the solution boils, the concentration of allylbromide drops.) After the two-hour addition, the mixture was kept at about 50° C. overnight. The next day the liquid was decanted and the solid washed with hexane. The liquid fractions were mixed and the solvents (hexane and toluene) were evaporated by rotary evaporation. The crude orange product was vacuum distilled (about 85° C. at 0.5 Torr) to give the intermediate product, the triethyleneglycol allyl methyl ether.

Scheme 1: The glycol, NaOH and the allylbromide are in a 1:1:1 molar ratio

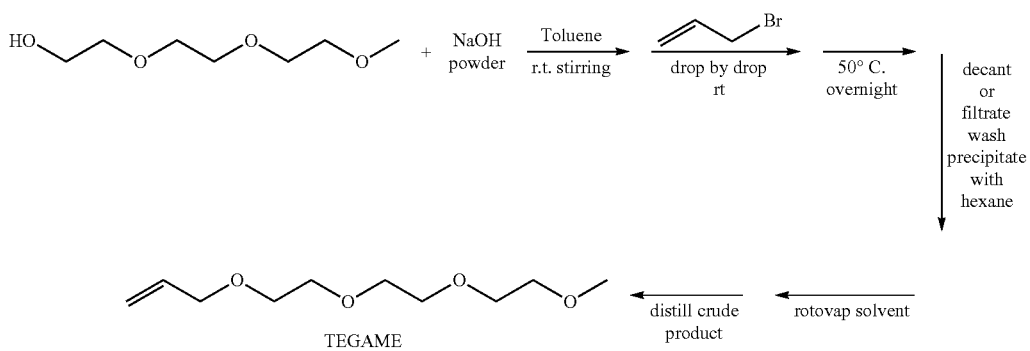

TEGAME

The next step involved the synthesis of the disiloxane 2S3D3 using a hydrosilylation reaction. See FIG. 1. This synthesis can also be accomplished under different conditions and using different catalysts. The route used here was as follows:

Triethyleneglycol allyl methyl ether (185 mL) was mixed with 66 g of 1,1,3,3-tetramethyldisiloxane and added approximately 100 uL of platinum(0)-1,3-divinyl-1,1,3,3-tetramethyldisiloxane complex solution in xylene, Pt ~2%. This was stirred at room temperature, with care taken that the solution did not boil. The mixture was then heated to about 50° C. overnight. In some runs, the disiloxane 2S3D3 was distilled (~240° C.; 1 Torr). In other runs, the disiloxane was used without further purification. See Scheme 2:

Scheme 2: The triethyleneglycol allyl methyl ether and the 1,1,3,3-tetramethyldisiloxane are in a 2:1 ratio

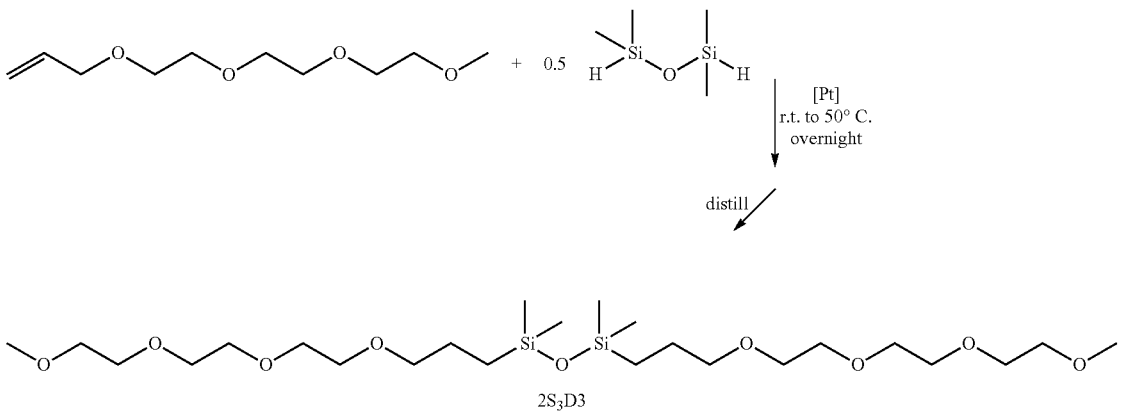

The Si—O—Si bond in 2S3D3 is then substituted with a halogen, in this example, fluorine. This can be done using $LiPF_6$, $NaF$, $NH_4F$, $NH_4FHF$, and the like. Any analogous halogen-containing compound (i.e., containing Cl or Br, rather than F) can be used.

265 g of 2S3D3 were mixed with 37 g of $LiPF_6$ and the mixture stirred to dissolve the salt. Then 4.5 g of water were added and the mixture was stirred overnight. The solution was then heated to about 80° C. for three hours to make it homogenous. The crude dark mixture was distilled three times to get pure F1S3M3. See FIG. 1 and Scheme 3:

Scheme 3: 2S3D3 and $LiPF_6$ are in a 1:2 ratio. (An excess of fluoride was used in this scheme)

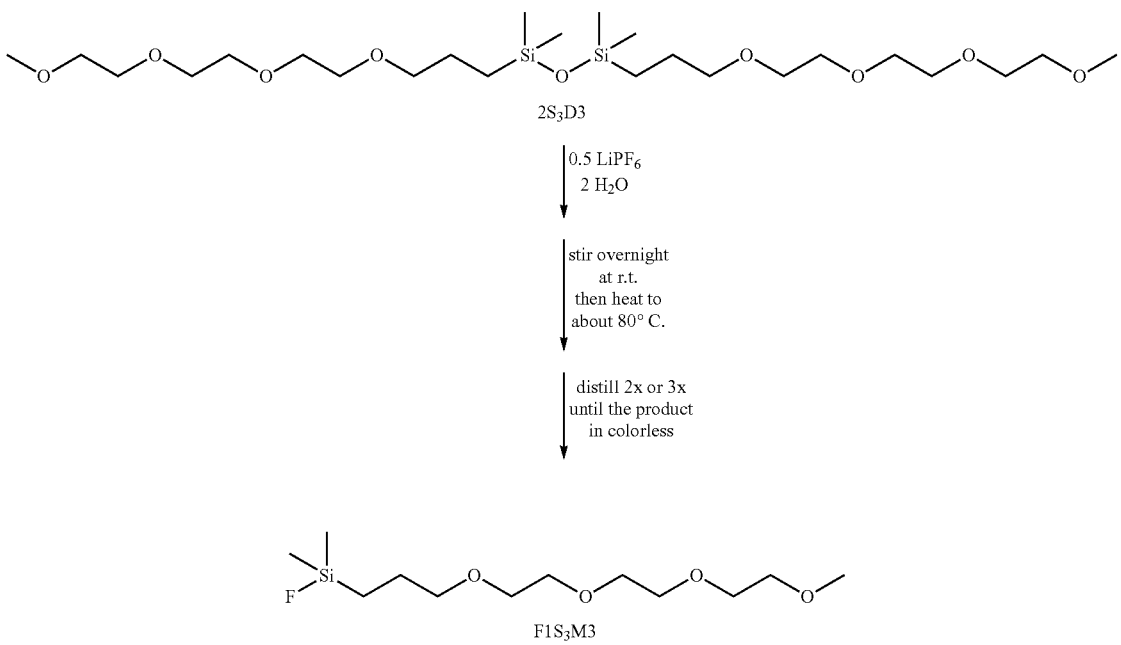

This same set of reactions can be used to make analogous compounds by using longer or shorter glycol units in Scheme 1, and altering the terminal moieties in the starting ether. Likewise, in Scheme 2, the 1,1,3,3-tetramethyldisiloxane can be replaced with other disiloxanes having a distinct substitution pattern, for example, different alkyl lengths, alkyloxy groups, etc. In the same fashion, the halogen-containing compound used to replace the Si—O—Si bond in 2S3D3 dictates the halogen atom that appears in the final product.

For example, see FIG. 2, which describes the analogous preferred synthesis of F1S3M2. Here, the initial hydrosilylation step takes place over a platinum catalyst to yield a chlorinated intermediate. The chloro intermediate is then treated with NH$_4$FHF (ammonium bifluoride) to yield the product F1S3M2 in good yield.

All analogous compounds as recited above can be fabricated using the synthetic approach presented in FIGS. 1 and 2 and using the appropriate starting material to arrive at the desired chain length of the spacer ($R^2$ and/or $R^3$), the desired side groups R and $R^1$, and the desired halogen X. In addition, one skilled in the art will recognize that alternate routes from reagents such as Me$_2$SiHF are equally viable.

Of particular note is that the compositions described herein have much improved thermal stability as compared to other Si-containing electrolytes such as 1NM3. See FIGS. 3A and 3B, which are graphs depicting the thermal stability of 1NM3 (FIG. 3A) versus the stability of F1S3M2 (FIG. 3B). ("1NM3"=(CH$_3$)$_3$—Si—O—(CH$_2$CH$_2$O)$_3$—CH$_3$) As shown in FIG. 3B, F1S3M2 displayed less than 5% decomposition after heating to 150° C. in the present of 1M LiPF$_6$. In stark contrast, as shown in FIG. 3A, 1NM3 displayed near-complete (~100%) at 100° C. in the presence of 1 M LiPF$_6$.

FIG. 4 is a graph depicting half cell cycling performance of compound F1S3M3 at 70° C., using a NMC cathode. The X-axis records cycle number, the Y-axis records specific capacity in mAhg. The specifics of the charge-discharge cycle and anode/cathode construction are recorded at the bottom of the figure. Of particular note in FIG. 4 is the very strong specific capacity of the F1S3M3 half cell after 50 charge/discharge cycles. The specific capacity for the F1S3M3 half cell after 50 charge/discharge cycles was still well above 100 mAhg. In contrast, the specific capacity of the 1NM3 half cell plummeted to close to zero after only 15 cycles. While the carbonate control half cell performed far better than the 1NM3 half cell, its performance was significantly worse than the F1S3M3 half cell after about 35 charge/discharge cycles.

The performance results were even more dramatic when comparing F1S3M3 at 70° C. using NCA cathodes. See FIG. 5. In this set of experiments, the carbonate control half cell and the F1 S3M3 half cell performed in near-parallel fashion. In contrast, the specific capacity of the 1NM3 half cell plummeted after approximately 10 cycles. This graph shows that the electrolyte composition described herein function quite well using different types of anodes, cathodes, and separators. Note that the FIG. 4 experiments used a half cell constructed of a NMC cathode, a lithium anode, and a W-Scope film separator. The F1S3M3 half cell performed admirably. The FIG. 5 experiments used a half cell constructed of a NCA cathode, a lithium anode, and a Celgard 2400 separator. The F1S3M3 half cell performed admirably under these conditions too.

In full cell cycling (F1S3M3EC), the compositions according to the present disclosure also fared well. See FIG. 5, which is a graph depicting full cell cycling performance of compound F1S3M3 at 70° C. using a NMC cathode. As shown in the figure, the F1S3M3 full cell equaled the performance of the carbonate control cell under these conditions. Similar results were obtained for F1S3M2 using a NCA cathode, as shown in FIG. 7. FIG. 7 is also notable because the discharge capacities followed identical trajectories whether at C/10 or C/2. In short, the electrolyte composition containing F1S3M2 performed in essentially identical fashion to the graphite control and the ECDEC control. (The graph depicted in FIG. 7 shows full cell cycling performance of F1S3M2 at 70° C. using a NCA cathode.)

FIG. 8 is similar to FIG. 7, but depicts full cell cycling performance of F1S3M2 at 55° C. using a NCA cathode. In the same fashion as in FIG. 7, the results are virtually indistinguishable between at both C/10 and C/2 as between the full cell containing the F1S3M2 electrolyte versus graphite control versus EC:DEC control. All results were indistinguishable. This is notable in that compositions according to the present disclosure are able to function at a host of different temperature conditions, using different anode and cathode materials, and different separators.

Lastly, see FIG. 9, which is a graph comparing discharge rates at 30° C. between F1S3M2 as compared to EC:DEC control device using a NCA cathode. As is clearly seen in FIG. 9, the discharge capacity of the F1S3M2 device closely mirrored that of the EC:DEC device at a host of different discharge conditions varying between C/10 to 2C during the course of the charge-discharge cycling. The results here are very significant in that the discharge rate was varied widely in cycles 1 to 8 (C/10, to C/4, to C/2, to C/1, to 2C, to C/10, and then held steady at C/4 from cycle 8 to cycle 17). The device including the electrolyte composition described herein performed in essentially the same fashion as the controls.

What is claimed is:

1. An electrolyte composition comprising at least one salt and at least one compound selected from the group consisting of:

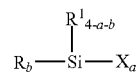

wherein subscript "a" is an integer of from 1 to 3;
subscript "b" is 1 or 2;
X is fluorine;
R is selected from the group consisting of Formula 1 moieties, and Formula II moieties:

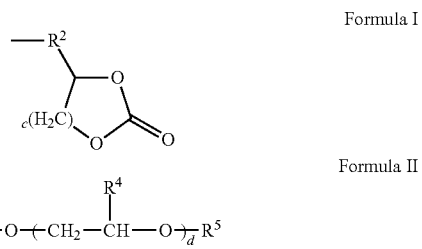

wherein $R^2$ is an organic spacer;
$R_3$ is nil or an organic spacer;
$R^4$ is hydrogen, alkyl, or aryl;
$R^5$ is alkyl or aryl;
subscript "c" is 1 or 2; and
subscript "d" is from 1 to 12; and
$R^1$ is selected from the group consisting of alkyl, substituted alkyl, aryl, and substituted aryl.

2. The electrolyte composition of claim 1, wherein $R^1$ is methyl.

3. The electrolyte composition according to claim 1, wherein the at least one salt is a lithium-containing salt.

4. The electrolyte composition according to claim 1, wherein the at least one salt is present in a concentration of from about 0.1 M to about 3.5 M.

5. The electrolyte composition according to claim 1, wherein the at least one salt is selected from the group consisting of $LiClO_4$, $LiBF_4$, $LiAsF_6$, $LiPF_6$, $LiCF_3SO_3$, $Li(CF_3SO_2)_2N$, $Li(CF_3SO_2)_3C$, $Li(C_2F_5SO_2)_2N$, LiDFOB, LiBOB, lithium alkyl fluorophosphates, lithium borates and lithium bis(chelato)borates.

6. The electrolyte composition according to claim 1, wherein the composition is a liquid.

7. The electrolyte composition according to claim 1, wherein the composition is a gel.

8. The electrolyte composition according to claim 1, wherein the composition is a solid.

9. An electrochemical device comprising an electrolyte composition as recited in claim 1.

10. The device of claim 9, wherein the electrochemical device includes an anode and the electrolyte composition further comprises an additive that forms a passivation layer on the anode.

11. The device of claim 9, wherein the device is a lithium secondary battery comprising at least one lithium metal oxide cathode and at least one anode.

12. A compound of formula:

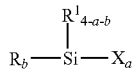

wherein subscript "a" is an integer of from 1 to 3;

subscript "b" is 1 or 2;

X is fluorine;

R is selected from the group consisting of Formula 1 moieties, and Formula II moieties:

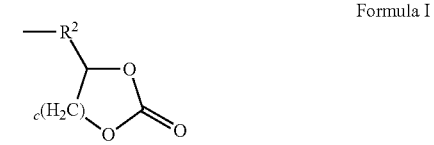

Formula I

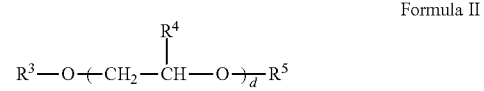

Formula II wherein $R^2$ is an organic spacer;

$R_3$ is nil or an organic spacer;

$R^4$ is hydrogen, alkyl, or aryl;

$R^5$ is alkyl or aryl;

subscript "c" is 1 or 2; and subscript "d" is from 1 to 12; and $R^1$ is selected from the group consisting of alkyl, substituted alkyl, aryl, and substituted aryl.

13. A compound of claim 12, wherein $R^1$ is methyl.

* * * * *